(12) United States Patent
Izumi

(10) Patent No.: US 7,230,897 B2
(45) Date of Patent: Jun. 12, 2007

(54) DEFECT DETECTION DEVICE

(75) Inventor: Teruhiko Izumi, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 507 days.

(21) Appl. No.: 10/899,008

(22) Filed: Jul. 27, 2004

(65) Prior Publication Data

US 2005/0030865 A1 Feb. 10, 2005

(30) Foreign Application Priority Data

Aug. 8, 2003 (JP) ............................. 2003-289620

(51) Int. Cl.
*G11B 7/00* (2006.01)
(52) U.S. Cl. .................................................. 369/53.15
(58) Field of Classification Search .................... None
See application file for complete search history.

(56) References Cited

U.S. PATENT DOCUMENTS

| | | | | |
|---|---|---|---|---|
| 4,832,487 A | * | 5/1989 | Mikuriya et al. | 369/53.13 |
| 5,027,339 A | * | 6/1991 | Yoda et al. | 369/53.15 |
| 5,357,497 A | * | 10/1994 | Ogawa | 369/53.15 |
| 5,777,967 A | * | 7/1998 | Ishibashi et al. | 369/59.2 |
| 6,172,953 B1 | * | 1/2001 | Kamiyama | 369/53.15 |
| 6,236,032 B1 | * | 5/2001 | Kamiyama | 369/43 |
| 6,791,916 B2 | * | 9/2004 | Tateishi et al. | 369/44.32 |
| 6,891,785 B2 | * | 5/2005 | Yamamoto et al. | 369/59.19 |
| 6,914,861 B2 | * | 7/2005 | Chou et al. | 369/59.16 |
| 2003/0128639 A1 | | 7/2003 | Kikuchi et al. | |

FOREIGN PATENT DOCUMENTS

JP 2003-196853 A 7/2003

\* cited by examiner

*Primary Examiner*—Thang V. Tran
(74) *Attorney, Agent, or Firm*—McDermott Will & Emery LLP

(57) ABSTRACT

The defect detection device includes: an amplification section for amplifying a reflection signal corresponding to the intensity of light reflected from an optical disc according to a control signal indicating recording or playback; an envelope detection section for outputting an envelope of the amplified signal; a first pulse generation section for outputting a pulse when the level of the control signal changes; an integration section for integrating the envelope; a differential signal generation section for receiving the envelope as a first input signal and the integrated results as a second input signal and outputting a differential signal corresponding to the difference between these signals; and a comparison section for comparing the differential signal with a predetermined value and outputting the results as a defect detection signal. The second input signal is changed so as to reduce the possibility that the defect detection signal may indicate the presence of a defect over the duration of the pulse.

6 Claims, 10 Drawing Sheets

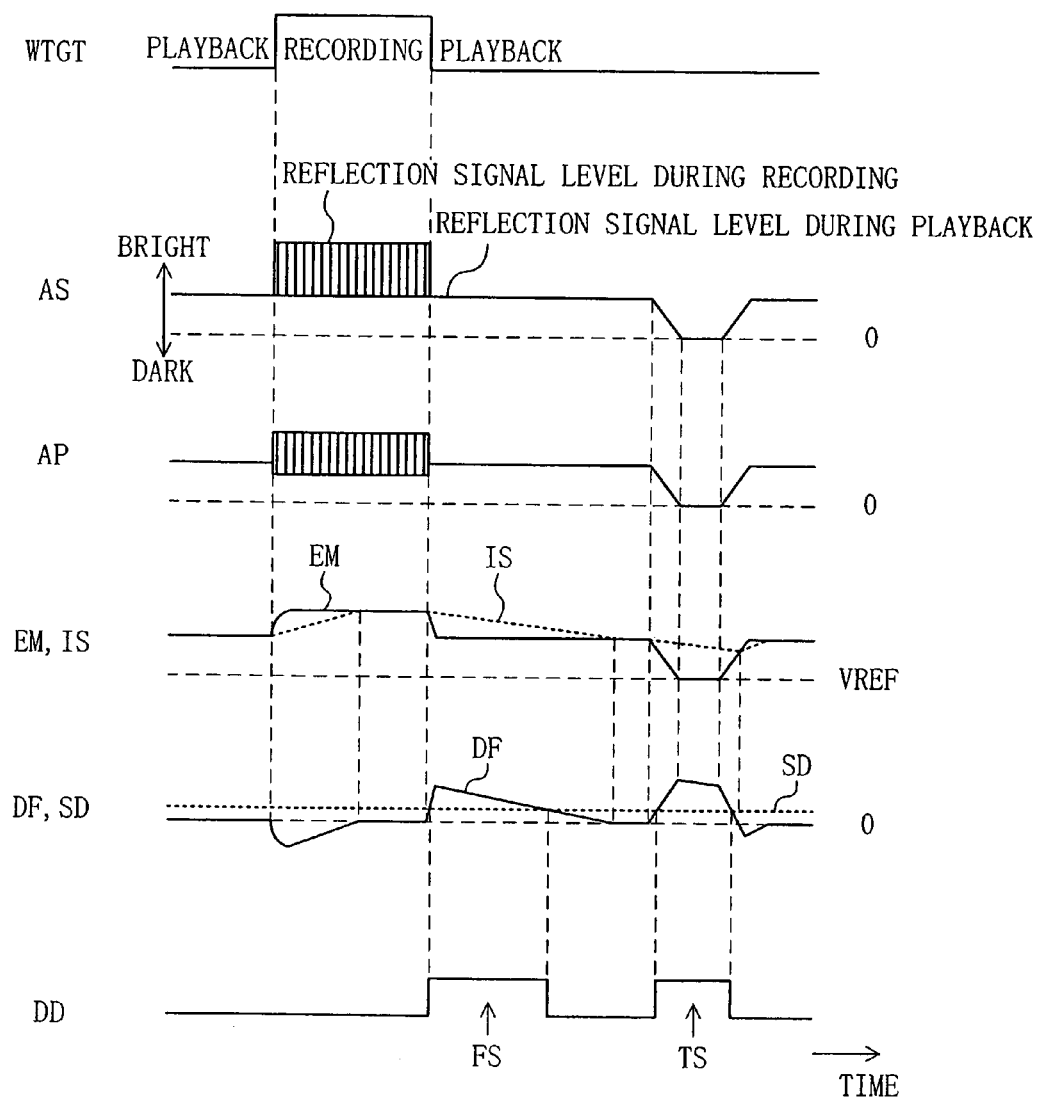

DEFECT DETECTION DEVICE

BACKGROUND OF THE INVENTION

The present invention relates to a defect detection device used for an optical disc apparatus and the like for detecting a defect (point where normal write/read operation fails) on an optical disc.

In recent years, in computer systems in which the information amount to be handled has substantially increased, large-capacity, high-speed optical disc apparatuses permitting random access operation have come into widespread use as recording/playback apparatuses for information data. These apparatuses use optical discs such as CD-R (compact disc recordable), CD-RW (CD rewritable), DVD-R/RW (digital versatile disc recordable/rewritable) and DVD-RAM (DVD random access memory), for example, as recording media.

A defect detection device used for an optical disc apparatus as described above generally detects a defect on an optical disc by converging a light beam on the optical disc and detecting a change in the envelope of a signal corresponding to the intensity of light reflected from the optical disc, and outputs a defect detection signal indicating the presence/absence of a defect. The defect detection signal may be used as a signal for holding a preceding value in a servo circuit that controls tracking and focusing servo for the optical disc, or used to obtain an extraction signal for determining a recording-prohibited region of the optical disc using a CPU incorporated in the optical disc apparatus for various controls.

FIG. 9 is a block diagram showing a construction of a conventional defect detection device. FIG. 10 is a graph showing the waveforms of signals used in the defect detection device of FIG. 9. The operation of the defect detection device of FIG. 9 is as follows.

A light beam is converged on an optical disc, and a reflection signal AS corresponding to the intensity of light reflected from the optical disc is input into a variable gain amplifier 902. The variable gain amplifier 902 amplifies the reflection signal AS with a gain corresponding to a recording gate signal WTGT indicating that it is during recording of data into the disc or during playback of data from the disc, to obtain a predetermined amplitude, and outputs the resultant signal to a high-speed envelope detection circuit 940. By this use of the variable gain amplifier 902, it is possible to prevent the difference in the level of light reflected from the disc between during recording and during playback from being detected as a change in envelope.

The high-speed envelope detection circuit 940 detects the envelope of the input signal, and outputs the results to a differential circuit 906 and an integration circuit 960. The integration circuit 960 integrates the output of the high-speed envelope detection circuit 940, and outputs the results to the differential circuit 906. For example, assume that the envelope of the reflection signal AS abruptly changes due to a defect present on an optical disc. An envelope signal EM output from the envelope detection circuit 940, of which the time constant is small, has a waveform following the abrupt change of the envelope, as shown in FIG. 10. On the contrary, an output signal IS of the integration circuit 960 has a smoothly changing waveform, in spite of the abrupt change of the reflection signal AS, as shown in FIG. 10.

The differential circuit 906 outputs a differential signal DF corresponding to the difference between the envelope signal EM and the output signal IS of the integration circuit 960 to a comparator 908. The comparator 908 digitizes the differential signal DF using a signal SD output from a D/A converter 912 as a slice level, to generate and output a defect detection signal DD (see Japanese Laid-Open Patent Publication No. 2003-196853, for example).

However, the device of FIG. 9 fails to eliminate the level difference in reflected light between during recording and during playback due to a variation in the setting of the gain of the variable gain amplifier 902 and other reasons. Therefore, at a shift of the operation for an optical disc from recording to playback or from playback to recording, a level difference arises in the output AP of the variable gain amplifier 902 as shown in FIG. 10.

In particular, when the operation for an optical disc shifts from recording to playback, while the envelope signal EM output from the envelope detection circuit 940 follows the level difference of the reflection signal AS, it takes time for the signal IS, obtained by integrating the envelope signal EM, to follow the level difference. The differential signal DF is therefore higher than the signal SD, and thus a false defect detection signal DD is output over a considerable time period (pulse FS in FIG. 10). As a result, highly stable playback is not achieved. When the operation for an optical disc shifts from playback to recording, correct defect detection is unattainable over a considerable time period although a false defect detection signal DD will not be output.

SUMMARY OF THE INVENTION

An object of the present invention is providing a defect detection device capable of detecting a defect on an optical disc further correctly for achievement of highly stable recording and playback.

Specifically, the defect detection device of the present invention includes: an amplification section for amplifying a reflection signal corresponding to the intensity of light reflected from an optical disc irradiated with a light beam, with a gain corresponding to a control signal indicating which is performed, recording or playback, for the optical disc, and outputting the amplified signal; an envelope detection section for obtaining an envelope of the output of the amplification section and outputting the obtained envelope; a first pulse generation section for outputting a pulse of a predetermined length when the level of the control signal changes; an integration section for integrating the output of the envelope detection section and outputting the integrated results; a differential signal generation section for receiving the output of the envelope detection section as a first input signal and the output of the integration section as a second input signal, generating a differential signal corresponding to a difference between the first input signal and the second input signal, and outputting the generated differential signal; and a comparison section for comparing the output of the differential signal generation section with a predetermined value, and outputting the results as a defect detection signal indicating the presence/absence of a defect, wherein the second input signal of the differential signal generation section is changed so as to reduce the possibility that the defect detection signal may indicate the presence of a defect during the time period for which the first pulse generation section outputs a pulse.

According to the invention described above, the possibility that the defect detection signal may indicate the presence of a defect is reduced during the time period for which the first pulse generation section outputs a pulse. This makes it possible to reduce the frequency at which a false defect detection signal indicating the presence of a defect is output although there is actually no defect immediately after switching of the operation for an optical disc to recording or playback.

The defect detection device described above preferably further includes a switch for selecting the signal output from the envelope detection section during the time period for which the first pulse generation section outputs a pulse and the signal output from the integration section during the remaining time period, and outputting the selected signal as the second input signal of the differential signal generation section.

According to the invention described above, the first and second input signals of the differential signal generation section are equal to each other during the time period for which the first pulse generation section outputs a pulse. This prevents a false defect detection signal from being output.

In the defect detection device described above, the integration section preferably reduces its time constant during the time period for which the first pulse generation section outputs a pulse.

According to the invention described above, the second input signal of the differential signal generation section swiftly follows the first input signal of the differential signal generation section. This makes it possible to reduce the frequency at which a false defect detection signal is output.

Preferably, the defect detection device described above further includes a second pulse generation section for outputting a pulse of a predetermined length once the pulse output from the first pulse generation section terminates, wherein the integration section has a first capacitor, one end of the first capacitor being grounded and the other end serving as the output of the integration section, and the integration section supplies a predetermined voltage to the first capacitor, the predetermined voltage having a value on the side of a level of the signal output from the envelope detection section when a defect is present with respect to a level of the signal output from the envelope detection section when no defect is present, during the time period for which the first pulse generation section outputs a pulse, and reduces the time constant of the integration section during the time period for which the second pulse generation section outputs a pulse.

According to the invention described above, it is possible to prevent a false defect detection signal from being output during the time period for which the first pulse generation section outputs a pulse. In addition, the time constant of the integration section is reduced during the time period for which the second pulse generation section outputs a pulse. This makes it possible to restart the defect detection soon after the termination of the time period during which the first pulse generation section outputs a pulse.

Preferably, the envelope detection section has a second capacitor, one end of the second capacitor being grounded and the other end serving as the output of the envelope detection section, and the envelope detection section supplies the predetermined voltage to the second capacitor during the time period for which the first pulse generation section outputs a pulse.

According to the invention described above, the same voltage as that supplied to the first capacitor of the integration section is supplied to the second capacitor of the envelope detection section during the time period for which the first pulse generation section outputs a pulse. Therefore, the differential signal generation section does not output a signal opposite in polarity to that output during defect detection. Since a narrow dynamic range is enough for the output of the differential signal generation section, the sensitivity of the defect detection can be enhanced.

Preferably, the integration section has a first switch for supplying the predetermined voltage to the first capacitor, the envelope detection section has a second switch for supplying the predetermined voltage to the second capacitor, and the envelope detection section is constructed so that the product of the capacitance of the first capacitor and the ON resistance of the first switch and the product of the capacitance of the second capacitor and the ON resistance of the second switch are substantially equal to each other.

According to the invention described above, the times required for the voltages at the first and second capacitors to reach a predetermined voltage during the time period for which the first pulse generation section outputs a pulse can be made roughly equal to each other. This ensures a narrow dynamic range for the output of the differential signal generation section.

As described above, according to the present invention, the possibility of outputting a false defect detection signal can be reduced, and thus a defect on an optical disc can be detected further correctly. As a result, highly stable recording and playback can be achieved.

BRIEF DESCRIPTION OF THE DRAWINGS

FIG. 10 is a graph showing the waveforms of signals used in the defect detection device of FIG. 9.

DESCRIPTION OF THE PREFERRED EMBODIMENTS

Hereinafter, preferred embodiments of the present invention will be described with reference to the accompanying drawings.

Embodiment 1

Figure 1:
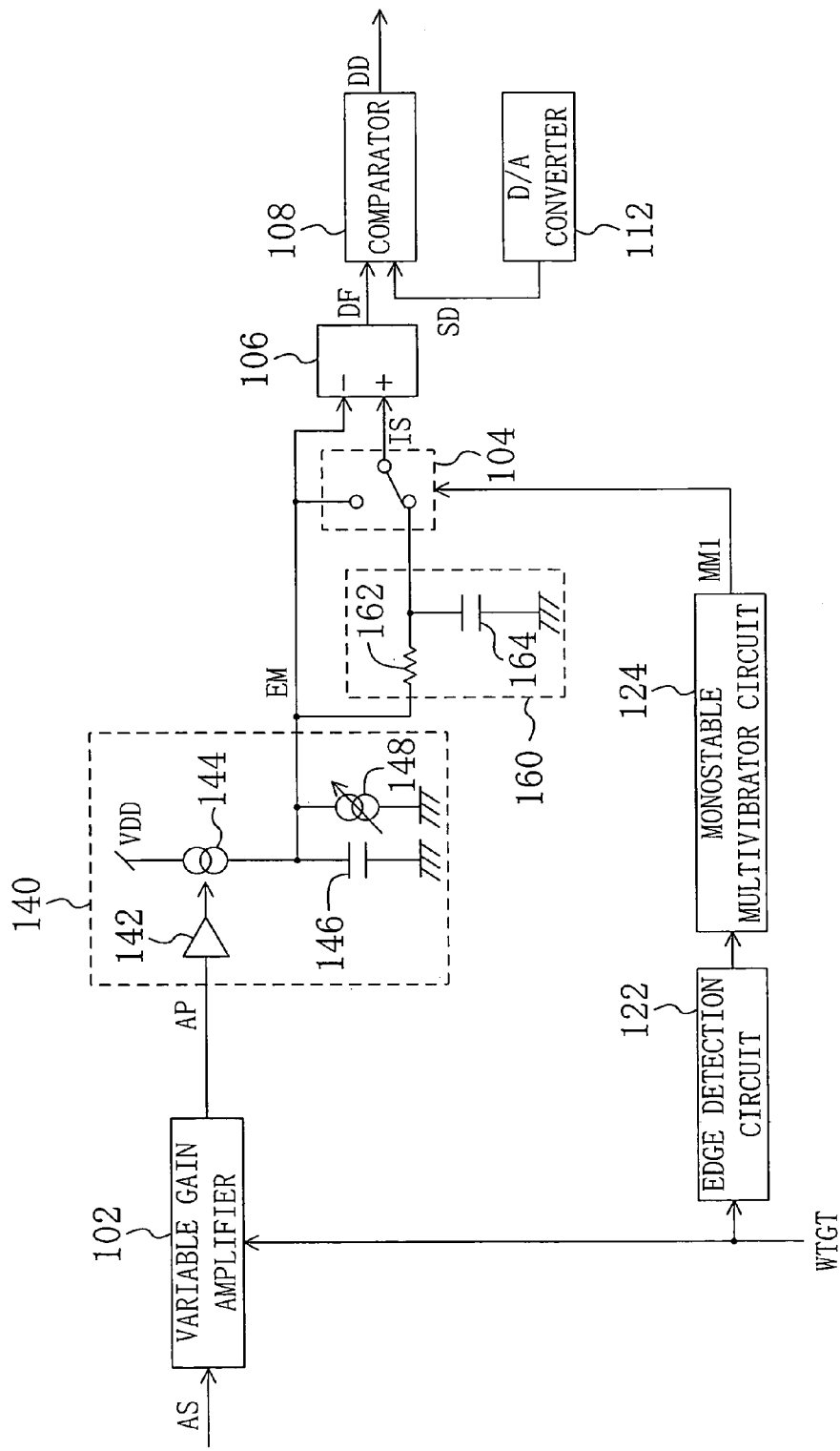
FIG. 1 is a block diagram showing a construction of a defect detection device of Embodiment 1 of the present invention.
Figure 2:
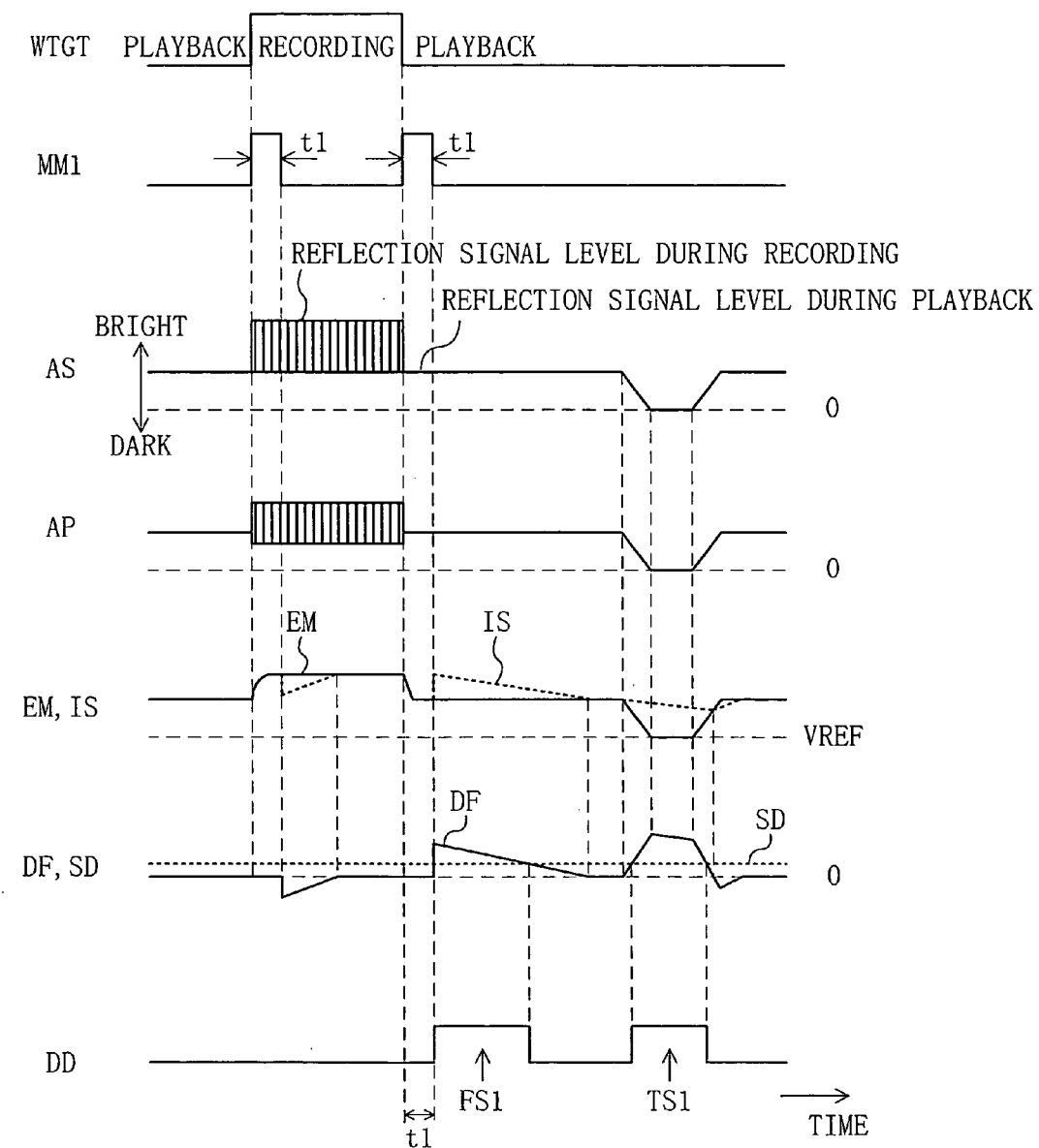
FIG. 2 is a graph showing the waveforms of signals used in the defect detection device of FIG. 1.

FIG. 1 is a block diagram showing a construction of a defect detection device of Embodiment 1 of the present invention. The defect detection device of FIG. 1 includes a variable gain amplifier 102 as the amplification section, a switch 104, a differential circuit 106 as the differential signal generation section, a comparator 108 as the comparison section, a D/A converter 112, an edge detection circuit 122, a monostable multivibrator circuit 124 as the first pulse generation section, a high-speed envelope detection circuit 140 as the envelope detection section, and an integration circuit 160 as the integration section. FIG. 2 is a graph showing the waveforms of signals used in the defect detection device of FIG. 1.

A light beam is converged on an optical disc and reflected from the optical disc. A plurality of light receiving elements (not shown) receive the reflected light and output electric signals corresponding to the intensity of the received light. The signals output from the plurality of light receiving elements are added together, and the resultant signal of the full addition is input into the variable gain amplifier 102 as a reflection signal AS.

The variable gain amplifier 102 also receives a recording gate signal WTGT. The recording gate signal WTGT, which is a signal indicating which operation, recording or playback, is being performed for the optical disc, is in a high logical state ("H") during recording and in a low logical state ("L") during playback, for example.

During recording, the light beam emitted to the optical disc is modulated so that the power changes from 15 mW at maximum to 0.5 mW at minimum, for example. During playback, the light beam is emitted with a comparatively small constant power. As the power of the light beam is greater and brighter, the level of the reflection signal AS is higher. Accordingly, a large difference arises in the level of the reflection signal AS between during playback and during recording (see FIG. 2). To minimize this difference, the variable gain amplifier 102 changes the gain with the recording gate signal WTGT. Specifically, the variable gain amplifier 102 amplifies the reflection signal AS with a small gain during recording and a large gain during playback, and outputs the resultant amplifier output signal AP to the high-speed envelope detection circuit 140.

The high-speed envelope detection circuit 140, which may be a general detection circuit, obtains the upper (bright-side) envelope of the amplifier output signal AP. The high-speed envelope detection circuit 140 includes an amplifier 142, current sources 144 and 148 and a capacitor 146. One end of the capacitor 146 is grounded, and the other end thereof serves as the output of the high-speed envelope detection circuit 140. In the high-speed envelope detection circuit 140, the current source 144 charges the capacitor 146 with a current of a magnitude corresponding to the amplifier output signal AP, and the current source 148 discharges the capacitor 146 with a current of a set magnitude. The high-speed envelope detection circuit 140 outputs the voltage at the capacitor 146 to the switch 104, the negative input terminal of the differential circuit 106, and the integration circuit 160, as the envelope signal EM.

The integration circuit 160 includes a resistance 162 and a capacitor 164. One end of the resistance 162 receives the envelope signal EM, and the other end thereof is connected to the switch 104 and also to one end of the capacitor 164. The other end of the capacitor 164 is grounded. Thus, the integration circuit 160 outputs a signal obtained by integrating the envelope signal EM to the switch 104.

The edge detection circuit 122 outputs a pulse to the monostable multivibrator circuit 124 every time the level of the recording gate signal WTGT changes. Once receiving a pulse from the edge detection circuit 122, the monostable multivibrator circuit 124 generates a pulse of being "H" for a time t1 of a predetermined length, and outputs this pulse to the switch 104 as a signal MM1.

The switch 104 selects the output of the integration circuit 160 when the signal MM1 is "L" and selects the envelope signal EM when it is "H", and outputs the selected signal to the positive input terminal of the differential circuit 106 as a signal IS.

The differential circuit 106 calculates the difference between the envelope signal EM as the input signal from the high-speed envelope detection circuit 140 and the signal IS as the input signal from the switch 104, and outputs the results to the comparator 108 as a differential signal DF.

The D/A converter 112, having a previously input digital value, converts this value to a voltage and outputs the voltage to the comparator 108 as a threshold SD. The comparator 108 compares the differential signal DF with the threshold SD, and outputs a signal of "H" when the differential signal DF is greater than the threshold SD and a signal of "L" when it is smaller than the threshold SD, as a defect detection signal DD. An arbitrary value may be given to the D/A converter 112, so that the threshold SD for the defect detection can be set freely.

The operation of the defect detection device of FIG. 1 observed when a defect is detected during playback, for example, will be described. Note that substantially the same operation will also be observed during recording. Assuming that some time has passed from a start of playback, the output signal MM1 of the monostable multivibrator circuit 124 is "L", and thus the switch 104 selects the output of the integration circuit 160.

When a defect is present on an optical disc, light reflected from the defect point of the optical disc is weak, and therefore the levels of the reflection signal AS and the amplifier output signal AP normally drop. The high-speed envelope detection circuit 140 follows the amplifier output signal AP of which the level drops due to the defect, and outputs the envelope signal EM having substantially the same level as the signal AP.

The integration circuit 160, of which the time constant is longer than that of the high-speed envelope detection circuit 160, does not follow the level drop of the envelope signal EM due to the defect. In other words, the output IS of the switch 104 that has selected the output of the integration circuit 160 little changes its level over the time period during which the level of the envelope signal EM is low due to the defect.

Accordingly, if a defect is present, a great change occurs in the differential signal DF output from the differential circuit 106 that calculates the difference between the output IS of the switch 104 and the envelope signal EM. The comparator 108 then outputs a pulse TS1 indicating detection of a defect, as the defect detection signal DD (see FIG. 2).

Next, the operation of the defect detection device of FIG. 1 observed when the operation for the optical disc is switched from recording to playback or from playback to recording, that is, the power of the light beam and the state of the optical disc apparatus are changed accordingly will be described. If the gain of the variable gain amplifier 102 is inappropriate due to a variation in the setting of the gain and the like, a difference may arise in the level of the envelope (upper envelope) of the amplifier output signal AP between during recording and during playback, as shown in FIG. 2.

If the level of the upper envelope of the amplifier output signal AP drops when the operation for the optical disc switches from recording to playback or from playback to recording, this will present substantially the same state as that observed when a defect is detected. Accordingly, the comparator 108 will output a pulse (false defect signal FS1) as the defect detection signal DD.

To avoid the occurrence described above, as shown in FIG. 2, the output signal MM1 of the monostable multivibrator circuit 124 is put in "H" for a time t1 after a change of the level of the recording gate signal WTGT, causing the switch 104 to select the envelope signal EM. This results in that the two input signals of the differential circuit 106 are the same signal and thus the differential signal DF output from the differential circuit 106 is zero. With the differential signal DF being kept smaller than the threshold SD, the defect detection signal DD output from the comparator 106 is kept "L". No false defect signal FS1 is thus generated. After the lapse of the time t1, the false defect signal FS1 will be generated. However, by extending the time t1 sufficiently, generation of the false defect signal FS1 can be prevented.

As described above, in the defect detection device of Embodiment 1, generation of a false defect signal is prevented during the time period for which the monostable multivibrator circuit 124 outputs a pulse. Therefore, the possibility of generating a false defect signal can be reduced.

Embodiment 2

Figure 3:
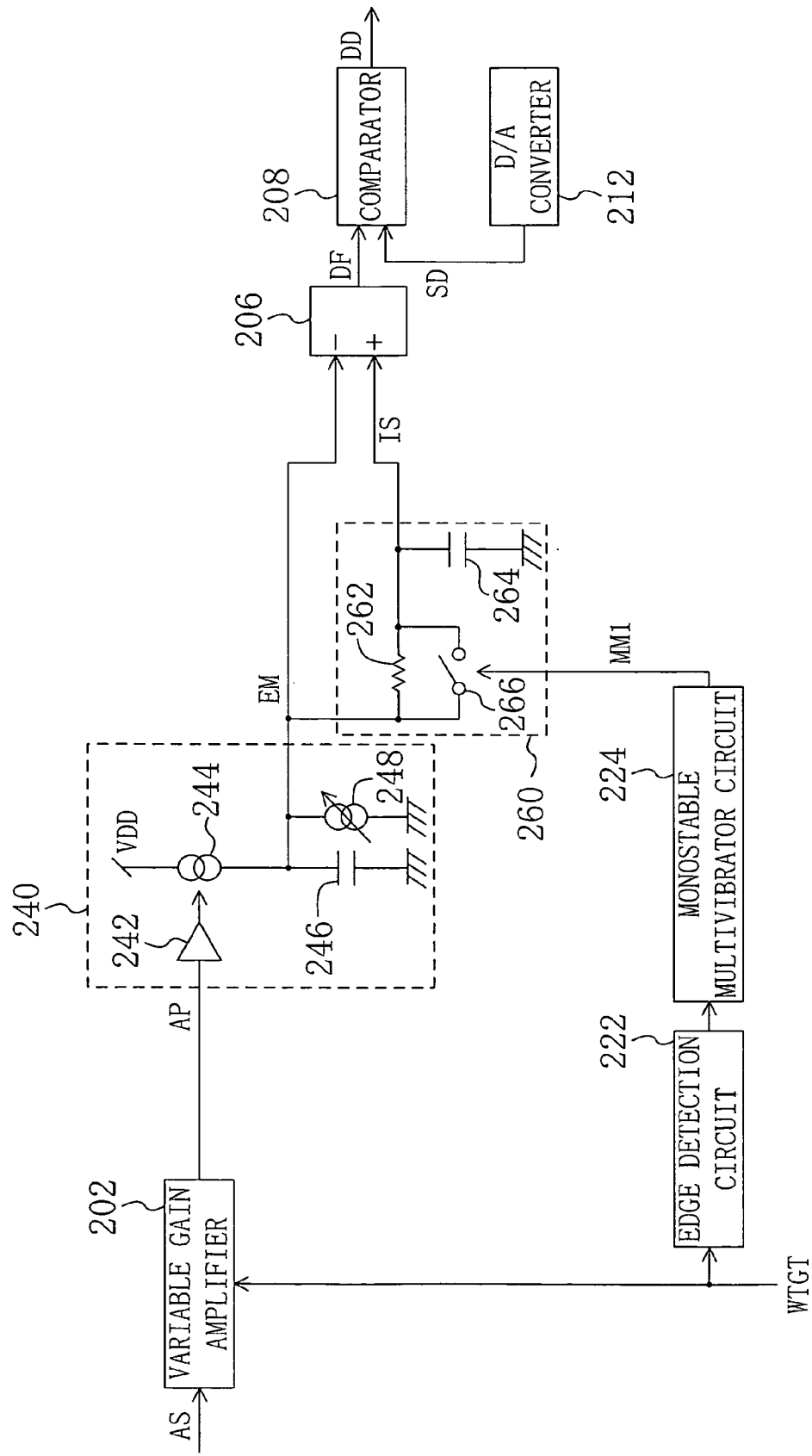
FIG. 3 is a block diagram showing a construction of a defect detection device of Embodiment 2 of the present invention.

FIG. 3 is a block diagram showing a construction of a defect detection device of Embodiment 2 of the present invention. The defect detection device of FIG. 3 is different from the defect detection device of FIG. 1 in that the switch 104 is omitted and that an integration circuit 260 is provided in place of the integration circuit 160.

Figure 4:
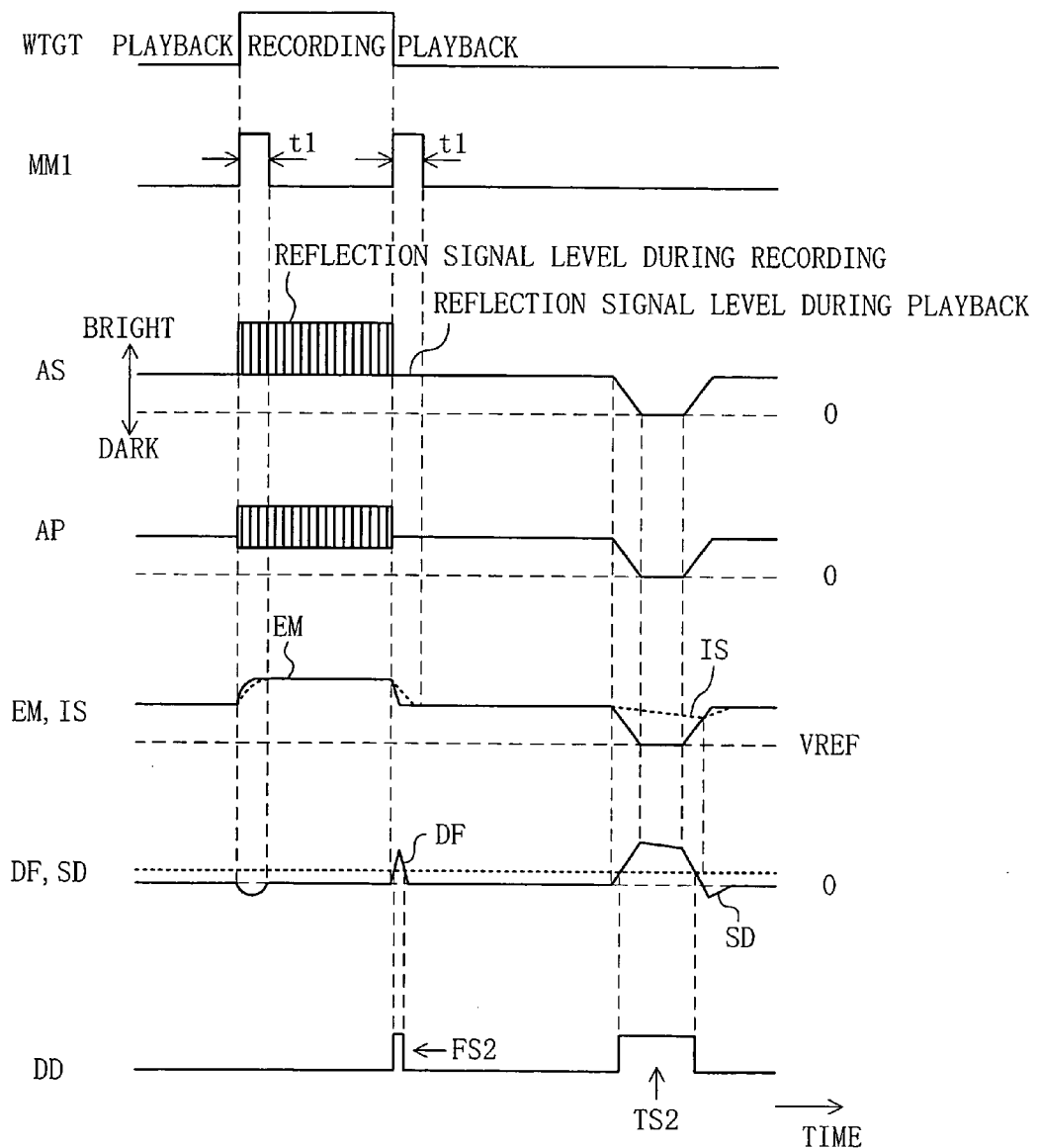
FIG. 4 is a graph showing the waveforms of signals used in the defect detection device of FIG.3.

The defect detection device of FIG. 3 also includes a variable gain amplifier 202, a differential circuit 206, a comparator 208, a D/A converter 212, an edge detection circuit 222, a monostable multivibrator circuit 224 and a high-speed envelope detection circuit 240, which are respectively substantially the same in construction as the variable gain amplifier 102, the differential circuit 106, the comparator 108, the D/A converter 112, the edge detection circuit 122, the monostable multivibrator circuit 124 and the high-speed envelope detection circuit 140. Description of these components is therefore omitted here. FIG. 4 is a graph showing the waveforms of signals used in the defect detection device of FIG. 3.

Referring to FIG. 3, the integration circuit 260 includes a resistance 262, a capacitor 264 and a switch 266. One end of the resistance 262 receives the envelope signal EM, and the other end thereof is connected to the positive input terminal of the differential circuit 206 and also to one end of the capacitor 264. The other end of the capacitor 264 is grounded. Thus, the integration circuit 260 outputs a signal obtained by integrating the envelope signal EM to the differential circuit 206 as the signal IS. The switch 266 is placed between both ends of the resistance 262. By operating the switch 266, therefore, the time constant of the integration circuit 260 can be switched. More specifically, the switch 266 is ON when the output signal MM1 of the monostable multivibrator circuit 224 is "H" and OFF when it is "L".

The differential circuit 206 calculates the difference between the envelope signal EM as the input signal from the high-speed envelope detection circuit 240 and the signal IS as the input signal from the integration circuit 260, and outputs the results to the comparator 208 as the differential signal DF.

The level of the recording gate signal WTGT changes with switching of the operation for an optical disc from recording to playback or from playback to recording. The monostable multivibrator circuit 224 puts its output signal MM1 in "H" for a time t1 after a change of the level of the recording gate signal WTGT. This causes the switch 266 to be ON and thus the time constant of the integration circuit 260 to be made small.

As a result, as shown in FIG. 4, the output signal IS of the integration circuit 260 changes fast to be close to the envelope signal EM. This suppresses the differential signal DF output from the differential circuit 206 from becoming so large, and thus widely shortens the time period during which a false defect signal FS2 is generated. If the time constant of the integration circuit 260 can be made sufficiently small, generation of the false defect signal FS2 itself can be prevented.

As described above, according to the defect detection device of Embodiment 2, the possibility of generation of a false defect signal can be reduced even immediately after switching of the operation for an optical disc from recording to playback or from playback to recording, by reducing the time constant of the integration circuit 260.

Embodiment 3

Figure 5:
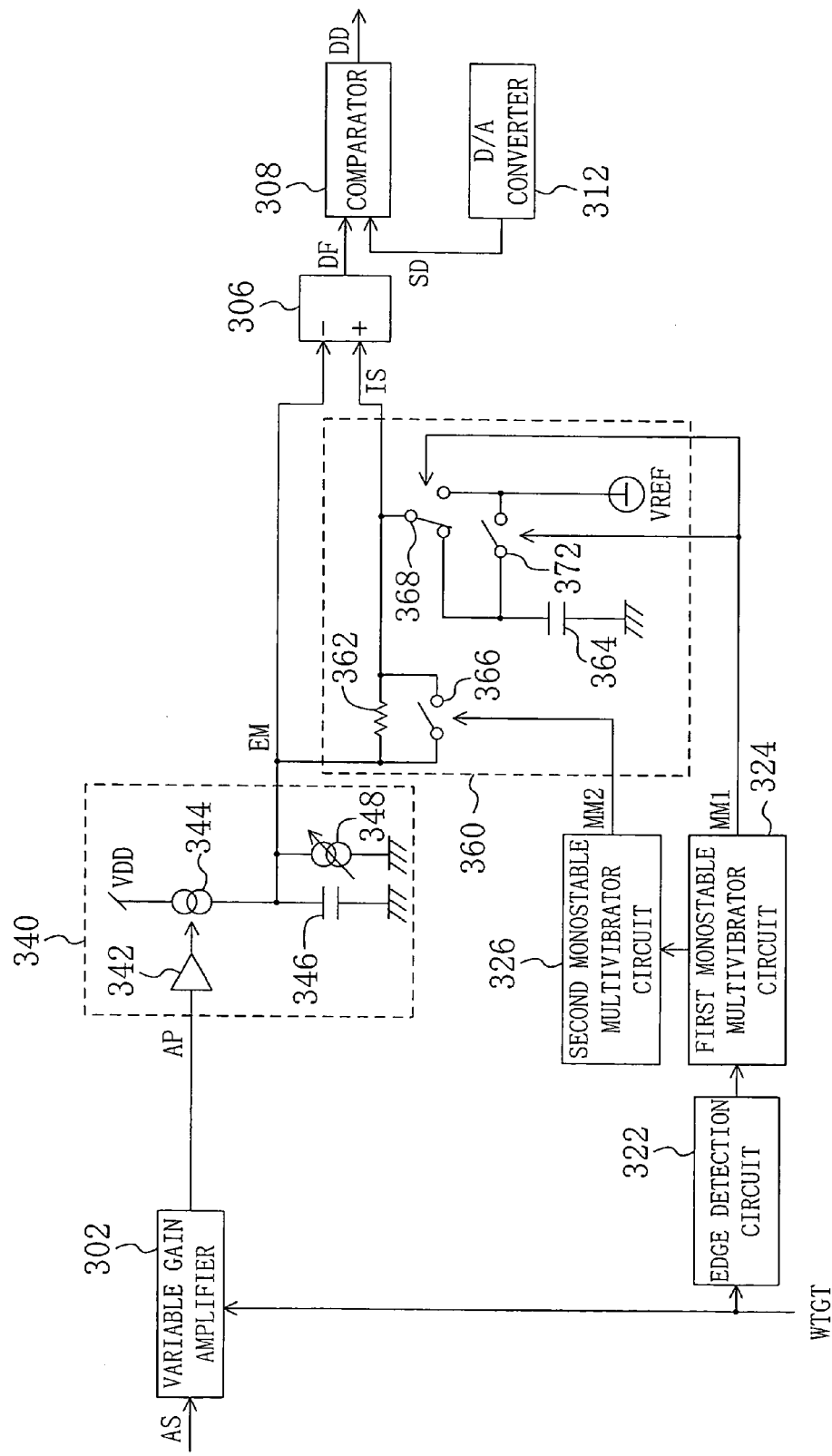
FIG. 5 is a block diagram showing a construction of a defect detection device of Embodiment 3 of the present invention.

FIG. 5 is a block diagram showing a construction of a defect detection device of Embodiment 3 of the present invention. The defect detection device of FIG. 5 is different from the defect detection device of FIG. 3 in that a second monostable multivibrator circuit 326 as the second pulse generation section is additionally provided and that an integration circuit 360 is provided in place of the integration circuit 260.

Figure 6:
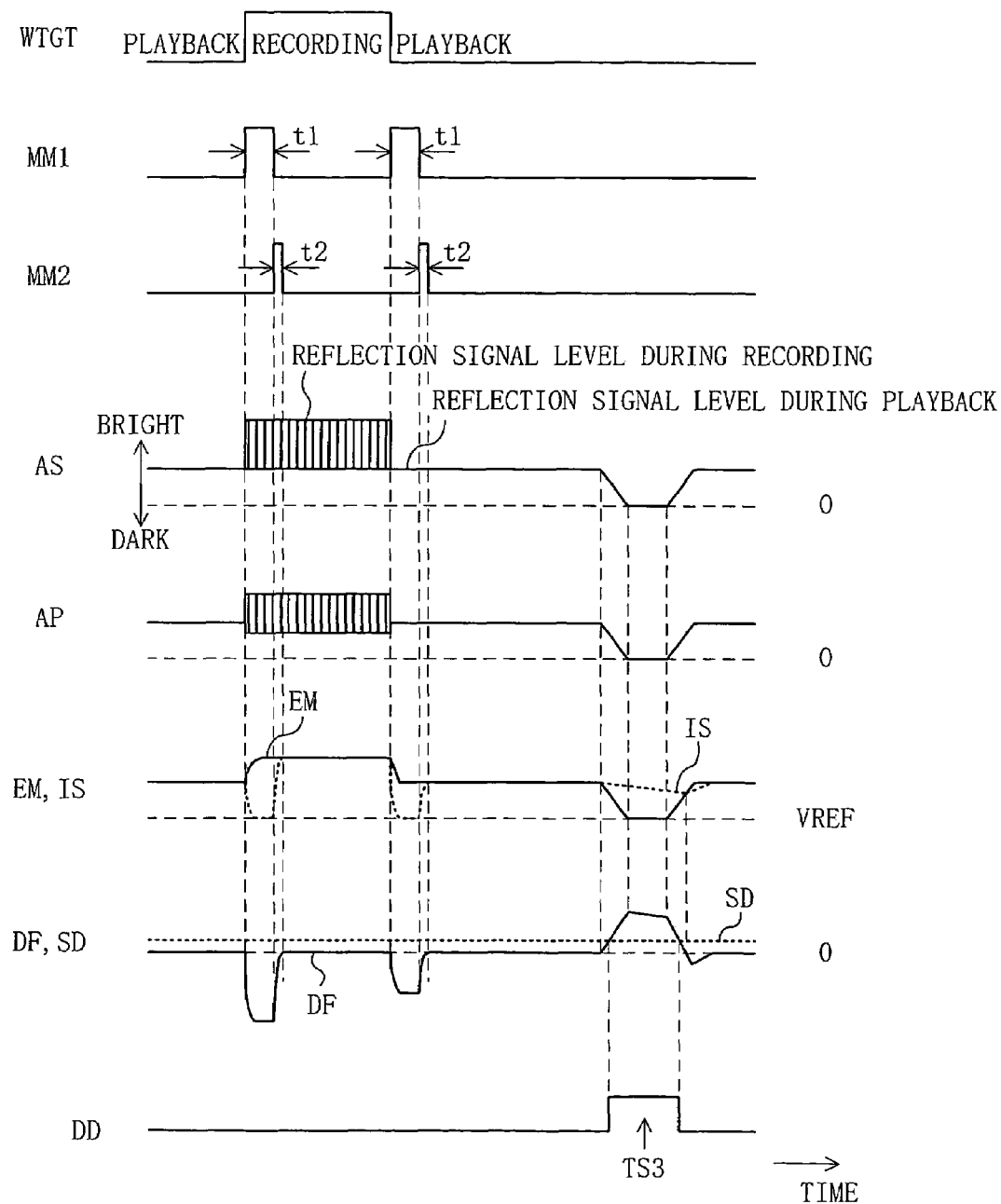
FIG. 6 is a graph showing the waveforms of signals used in the defect detection device of FIG. 5.

The defect detection device of FIG. 5 also includes a variable gain amplifier 302, a differential circuit 306, a comparator 308, a D/A converter 312, an edge detection circuit 322, a first monostable multivibrator circuit 324 and a high-speed envelope detection circuit 340, which are respectively substantially the same in construction as the variable gain amplifier 202, the differential circuit 206, the comparator 208, the D/A converter 212, the edge detection circuit 222, the monostable multivibrator circuit 224 and the high-speed envelope detection circuit 240. Description of these components is therefore omitted here. FIG. 6 is a graph showing the waveforms of signals used in the defect detection device of FIG. 5.

Referring to FIG. 5, the first monostable multivibrator circuit 324 outputs its output signal MM1 to the second monostable multivibrator circuit 326 and the integration circuit 360. The second monostable multivibrator circuit 326 outputs its output signal MM2 to the integration circuit 360. The second monostable multivibrator circuit 326 generates and outputs a pulse of being "H" for a time t2 of a predetermined length once the pulse output from the first monostable multivibrator circuit 324 terminates, that is, once the level of the signal MM1 changes from "H" to "L" (see FIG. 6).

The integration circuit 360 includes a resistance 362, a capacitor 364 and switches 366, 368 and 372. One end of the resistance 362 receives the envelope signal EM, and the other end thereof is connected to the positive input terminal of the differential circuit 306 and also to one end of the capacitor 364 via the switch 368. The other end of the capacitor 364 is grounded. Thus, the integration circuit 360 outputs a signal obtained by integrating the envelope signal EM to the differential circuit 306 as the signal IS.

The switch 368 selects the capacitor 364 when the signal MM1 is "L" and a reference voltage VREF when it is "H", to connect the selected one to the positive input terminal of the differential circuit 306. The switch 372 is ON only when the signal MM1 is "H", to supply the reference voltage VREF to the capacitor 364. The switch 366 is placed between both ends of the resistance 362. By operating the switch 366, therefore, the time constant of the integration circuit 360 is switched. More specifically, the switch 366 is ON when the output signal MM2 of the second monostable multivibrator circuit 326 is "H" and OFF when it is "L".

The differential circuit 306 calculates the difference between the envelope signal EM as the input signal from the high-speed envelope detection circuit 340 and the signal IS as the input signal from the integration circuit 360, and outputs the results to the comparator 308 as the differential signal DF.

The level of the recording gate signal WTGT changes with switching of the operation for an optical disc from recording to playback or from playback to recording. As shown in FIG. 6, the first monostable multivibrator circuit 324 puts its output signal MM1 in "H" for a time t1 after a change of the level of the recording gate signal WTGT. With the signal MM1 being "H", the switch 368 selects the reference voltage VREF, and thus the reference voltage VREF is output from the integration circuit 360 as the signal IS. Also, the switch 372 is made ON to supply the reference voltage VREF to the capacitor 364, so that the voltage at the capacitor 364 is initialized to the reference voltage VREF.

The reference voltage VREF is a voltage having a value on the side of the level of the envelope signal EM observed when a defect is present with respect to the level of the envelope signal EM observed when no defect is present. Herein, the reference voltage VREF is set at a value lower than the voltage of the envelope signal EM.

The second monostable multivibrator circuit 326 puts its output signal MM2 in "H" for a time t2 after termination of a pulse output from the first monostable multivibrator circuit 324. With the signal MM2 being "H", the switch 366 is made ON to reduce the time constant of the integration circuit 360.

As a result, as shown in FIG. 6, the output signal IS of the integration circuit 360 is fixed to a low voltage during the time period for which the first monostable multivibrator circuit 324 outputs a pulse, and thereafter rapidly goes closer to the envelope signal EM during the time period for which the second monostable multivibrator circuit 326 outputs a pulse. In other words, during the time t1+t2, the differential signal DF output from the differential circuit 306 changes its level in the direction opposite to that in which it changes when a defect is detected (that is, toward a negative voltage). Accordingly, the comparator 308 is prevented from generating a false defect signal.

As described above, according to the defect detection device of Embodiment 3, generation of a false defect signal is prevented even immediately after switching of the operation for an optical disc from recording to playback or from playback to recording, by fixing the output signal IS of the integration circuit 360 at a low level and thereafter reducing the time constant of the integration circuit 360. Thus, highly reliable defect detection free from false detection can be achieved.

Embodiment 4

Figure 7:
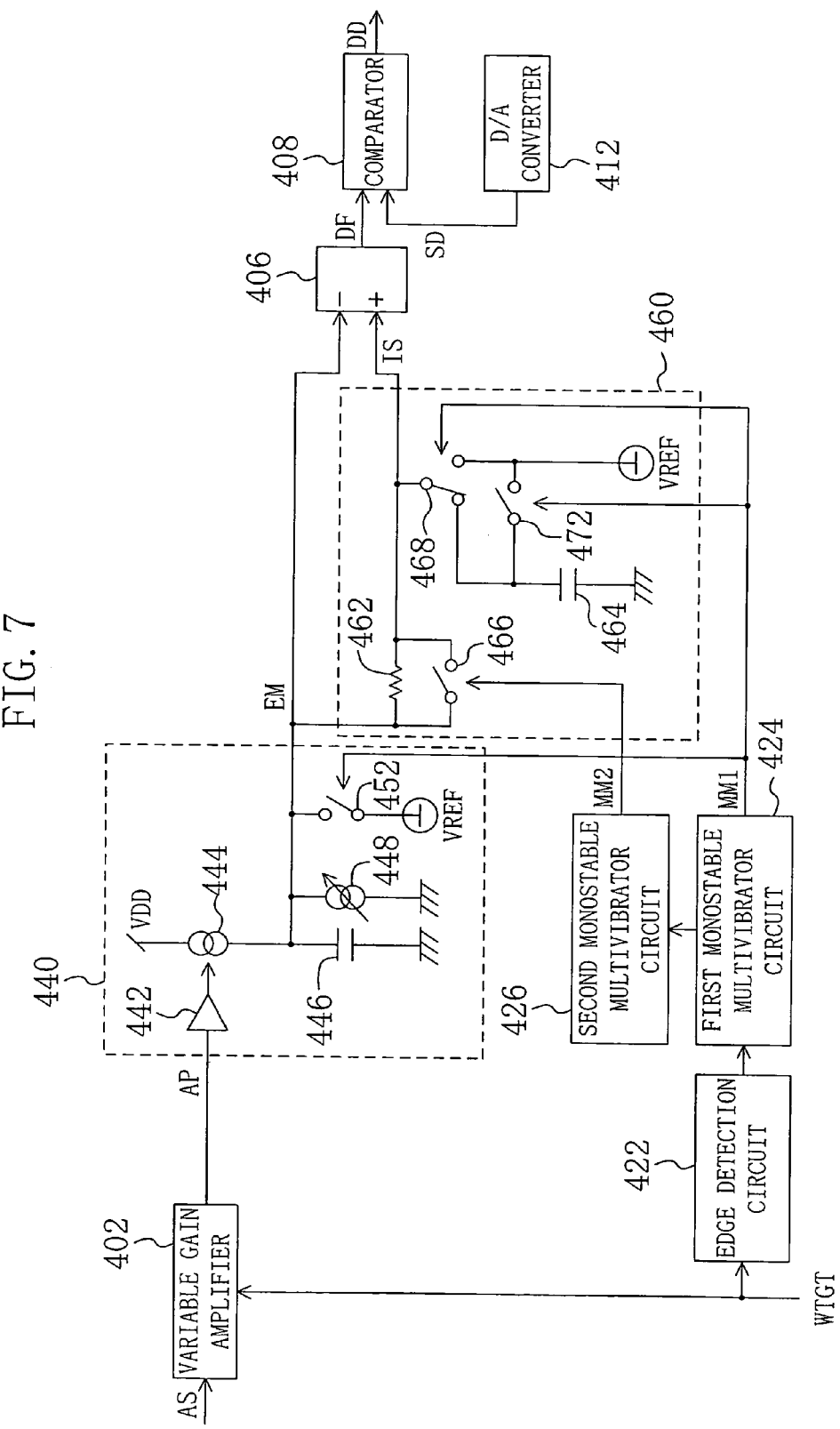
FIG. 7 is a block diagram showing a construction of a defect detection device of Embodiment 4 of the present invention.

FIG. 7 is a block diagram showing a construction of a defect detection device of Embodiment 4 of the present invention. The defect detection device of FIG. 7 is different from the defect detection device of FIG. 5 in that a high-speed envelope detection circuit 440 is provided in place of the high-speed envelope detection circuit 340.

The defect detection device of FIG. 7 also includes a variable gain amplifier 402, a differential circuit 406, a comparator 408, a D/A converter 412, an edge detection circuit 422, a first monostable multivibrator circuit 424, a second monostable multivibrator circuit 426 and an integration circuit 460, which are respectively substantially the same in construction as the variable gain amplifier 302, the differential circuit 306, the comparator 308, the D/A converter 312, the edge detection circuit 322, the first monostable multivibrator circuit 324, the second monostable multivibrator circuit 326 and the integration circuit 360. Description of these components is therefore omitted here.

Figure 8:
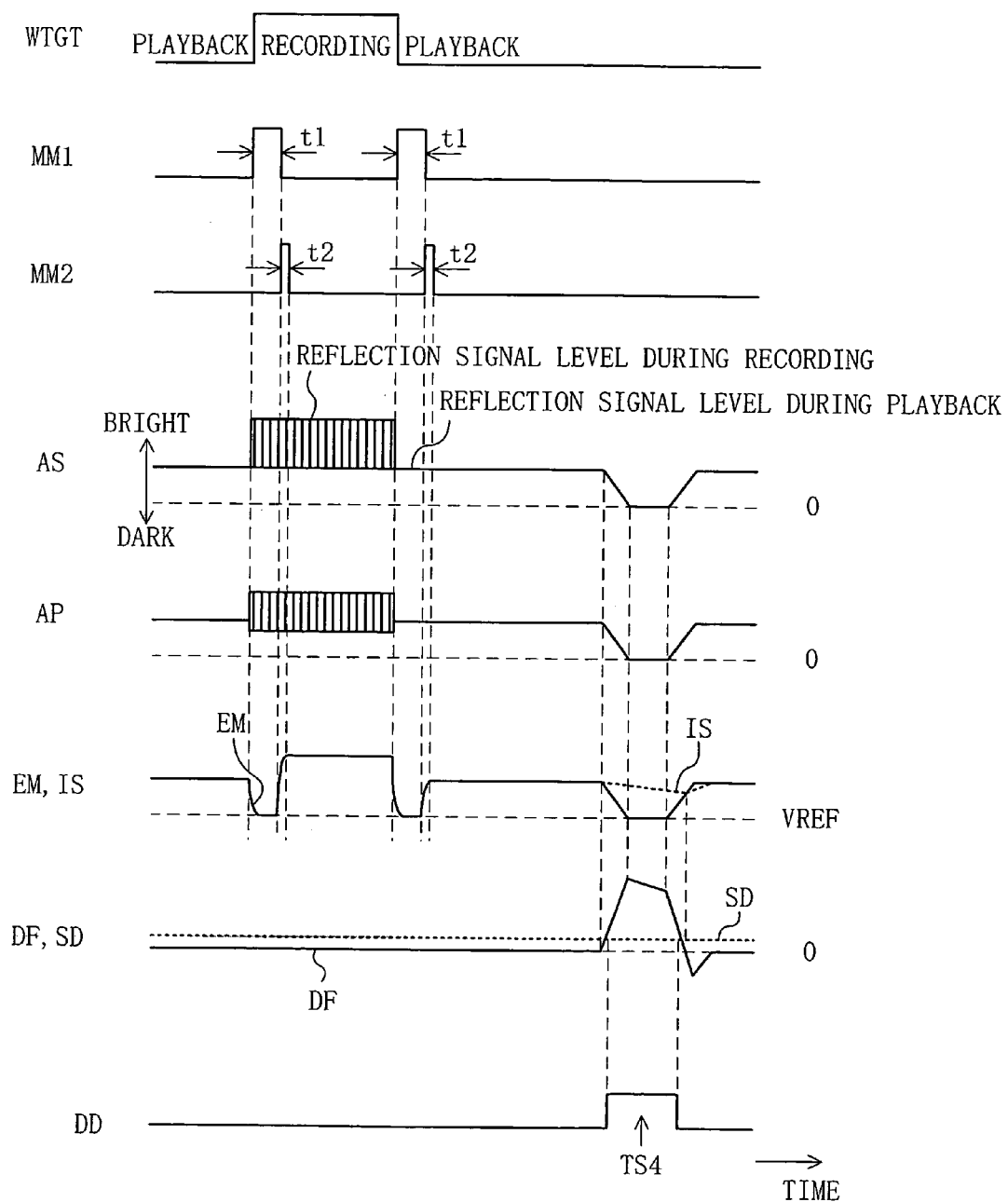
FIG. 8 is a graph showing the waveforms of signals used in the defect detection device of FIG. 7.
Figure 9:
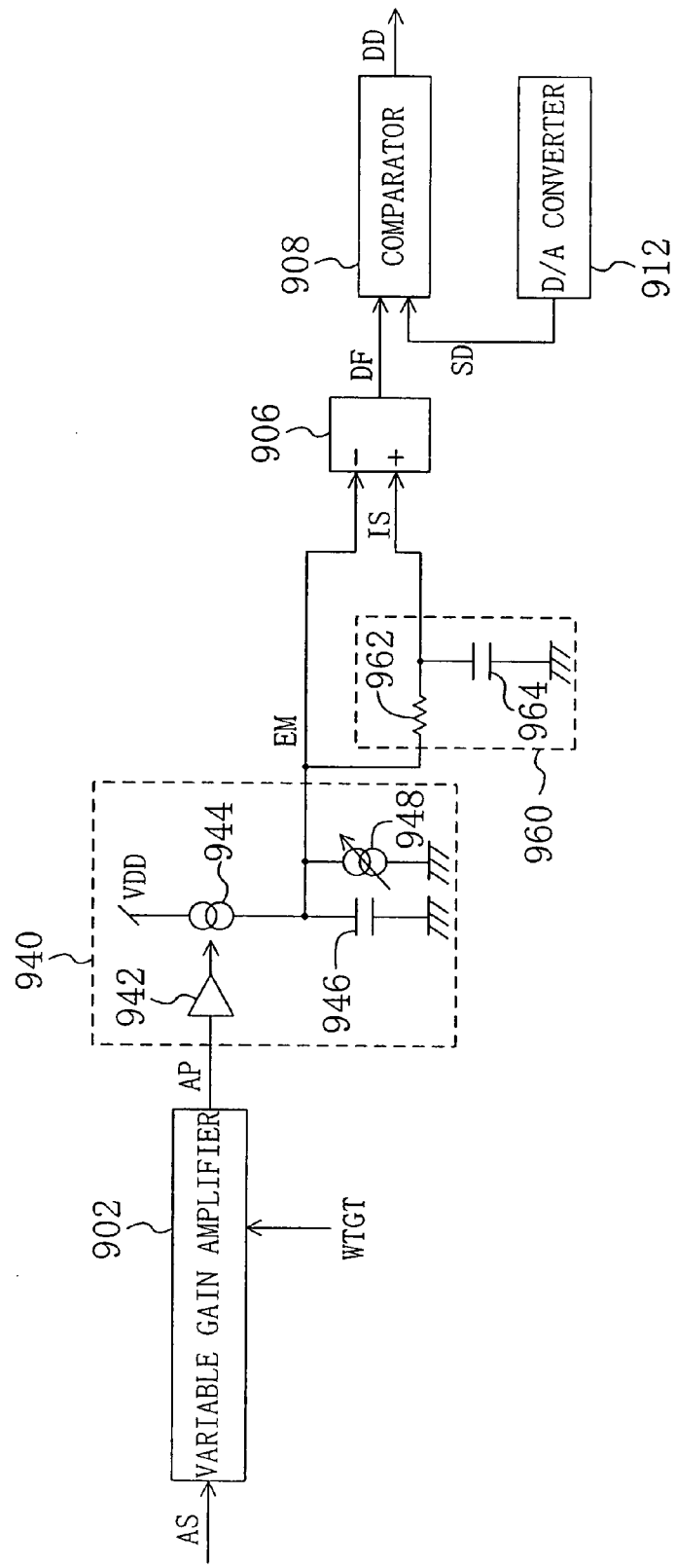
FIG. 9 is a block diagram showing a construction of a conventional defect detection device.

FIG. 8 is a graph showing the waveforms of signals used in the defect detection device of FIG. 7.

The integration circuit 460 includes a resistance 462, a capacitor (first capacitor) 464 and switches 466, 468 and 472, which are respectively substantially the same in construction as the resistance 362, the capacitor 364 and the switches 366, 368 and 372. The switch 472 constitutes a first switch.

The high-speed envelope detection circuit 440 is different from the high-speed envelope detection circuit 140 in FIG. 1 in that a switch (second switch) 452 is newly provided. The high-speed envelope detection circuit 440 also includes an amplifier 442, current sources 444 and 448, and a capacitor (second capacitor) 446, which are respectively substantially the same in construction as the amplifier 142, the current sources 144 and 148, and the capacitor 146.

The switch 452 is operable to supply the reference voltage VREF to the output of the high-speed envelope detection circuit 440, that is, to the capacitor 446 only when the level of the output signal MM1 of the first monostable multivibrator circuit 424 is "H".

The level of the recording gate signal WTGT changes with switching of the operation for an optical disc from recording to playback or from playback to recording. As shown in FIG. 8, the first monostable multivibrator circuit 424 puts its output signal MM1 in "H" for a time t1 after a change of the level of the recording gate signal WTGT. With the signal MM1 being "H", the switch 452 is made ON, allowing the voltage at the capacitor 446, that is, the envelope signal EM output from the high-speed envelope detection circuit 440 to be initialized to the reference voltage VREF. Thereafter, as the switch 452 is turned OFF, the envelope signal EM rapidly resumes its original value.

As a result, as shown in FIG. 8, the envelope signal EM is substantially equal in level to the output signal IS of the integration circuit 460 during the time period (time t1+t2) for which the first and second monostable multivibrator circuit 424 and 426 output their pulses. Accordingly, the output of the differential circuit 406 is substantially zero, and thus the comparator 408 is prevented from generating a false defect signal.

Also, during the above time period, the differential circuit 406 does not output a signal opposite in polarity to that output when a defect is detected (signal having a negative value). Accordingly, the dynamic range of the output is prevented from becoming wide, and thus in the D/A converter 412 that outputs the threshold SD to the comparator 408, the quantization step size can be made small without changing the resolution (the number of bits of the input digital value). Since the threshold SD can be set more appropriately, the sensitivity of the defect detection can be enhanced.

The switches 452 and 472 have a resistance (ON resistance) even when they are ON. Therefore, the voltages at the capacitors 446 and 464 gradually decrease during the initialization of the capacitors with a pulse of the signal MM1. Since the voltages at the capacitors 446 and 464 are given to the differential circuit 406, they should desirably be equal to each other at least until termination of a pulse of the signal MM1.

In view of the above, the high-speed envelope detection circuit 440 and the integration circuit 460 may be constructed so that the product of the capacitance of the capacitor 446 and the ON resistance of the switch 452 and the product of the capacitance of the capacitor 464 and the ON resistance of the switch 472 are substantially equal to each other.

As described above, according to the defect detection device of Embodiment 4, generation of a false defect signal is prevented even immediately after switching of the operation for an optical disc from recording to playback or from playback to recording, by fixing the envelope signal EM output from the high-speed envelope detection circuit 440 and the output signal IS of the integration circuit 460 at a low level and thereafter reducing the time constant of the integration circuit 460. Thus, highly reliable defect detection free from false detection can be achieved. In addition, the sensitivity of the defect detection can be enhanced.

As described above, the defect detection device of the present invention can detect a defect on an optical disc further correctly, and is useful as a defect detection device and the like used in an optical disc apparatus and the like.

While the present invention has been described in preferred embodiments, it will be apparent to those skilled in the art that the disclosed invention may be modified in numerous ways and may assume many embodiments other than that specifically set out and described above. Accordingly, it is intended by the appended claims to cover all modifications of the invention which fall within the true spirit and scope of the invention.

What is claimed is:

1. A defect detection device comprising:
    an amplification section for amplifying a reflection signal corresponding to the intensity of light reflected from an optical disc irradiated with a light beam, with a gain corresponding to a control signal indicating which is performed, recording or playback, for the optical disc, and outputting the amplified signal;
    an envelope detection section for obtaining an envelope of the output of the amplification section and outputting the obtained envelope;
    a first pulse generation section for outputting a pulse of a predetermined length when the level of the control signal changes;
    an integration section for integrating the output of the envelope detection section and outputting the integrated results;
    a differential signal generation section for receiving the output of the envelope detection section as a first input signal and the output of the integration section as a second input signal, generating a differential signal corresponding to a difference between the first input signal and the second input signal, and outputting the generated differential signal; and
    a comparison section for comparing the output of the differential signal generation section with a predetermined value, and outputting the results as a defect detection signal indicating the presence/absence of a defect,
    wherein the second input signal of the differential signal generation section is changed so as to reduce the possibility that the defect detection signal may indicate the presence of a defect during the time period for which the first pulse generation section outputs a pulse.

2. The defect detection device of claim 1, further comprising a switch for selecting the signal output from the envelope detection section during the time period for which the first pulse generation section outputs a pulse and the signal output from the integration section during the remaining time period, and outputting the selected signal as the second input signal of the differential signal generation section.

3. The defect detection device of claim 1, wherein the integration section reduces its time constant during the time period for which the first pulse generation section outputs a pulse.

4. The defect detection device of claim 1, further comprising a second pulse generation section for outputting a pulse of a predetermined length once the pulse output from the first pulse generation section terminates,
    wherein the integration section has a first capacitor, one end of the first capacitor being grounded and the other end serving as the output of the integration section, and the integration section supplies a predetermined voltage to the first capacitor, the predetermined voltage having a value on the side of a level of the signal output from the envelope detection section when a defect is present with respect to a level of the signal output from the envelope detection section when no defect is present, during the time period for which the first pulse generation section outputs a pulse, and reduces the time constant of the integration section during the time period for which the second pulse generation section outputs a pulse.

5. The defect detection device of claim 4, wherein the envelope detection section has a second capacitor, one end of the second capacitor being grounded and the other end serving as the output of the envelope detection section, and the envelope detection section supplies the predetermined voltage to the second capacitor during the time period for which the first pulse generation section outputs a pulse.

6. The defect detection device of claim 5, wherein the integration section has a first switch for supplying the predetermined voltage to the first capacitor,
    the envelope detection section has a second switch for supplying the predetermined voltage to the second capacitor, and
    the envelope detection section is constructed so that the product of the capacitance of the first capacitor and the ON resistance of the first switch and the product of the capacitance of the second capacitor and the ON resistance of the second switch are substantially equal to each other.

* * * * *